(12) United States Patent
Waldron et al.

(10) Patent No.: US 8,637,495 B2
(45) Date of Patent: Jan. 28, 2014

(54) OSTEOARTHRITIS DIET FORMULATIONS

(75) Inventors: Mark K. Waldron, Sunset Hill, MO (US); Steven S. Hannah, Chesterfield, MO (US)

(73) Assignee: Nestec S.A., Vevey (CH)

(*) Notice: Subject to any disclaimer, the term of this patent is extended or adjusted under 35 U.S.C. 154(b) by 797 days.

(21) Appl. No.: 11/173,360

(22) Filed: Jul. 1, 2005

(65) Prior Publication Data

US 2006/0024356 A1 Feb. 2, 2006

Related U.S. Application Data

(60) Provisional application No. 60/584,703, filed on Jul. 1, 2004.

(51) Int. Cl.
*A61K 31/202* (2006.01)
*A61K 31/225* (2006.01)

(52) U.S. Cl.
USPC .......................................... 514/183; 514/547

(58) Field of Classification Search
USPC .................................................. 514/183, 547
See application file for complete search history.

(56) References Cited

U.S. PATENT DOCUMENTS

| | | | | |
|---|---|---|---|---|
| 4,282,265 A * | 8/1981 | Theuer | .......................... | 426/607 |
| 5,013,569 A * | 5/1991 | Rubin | .......................... | 426/585 |
| 5,434,183 A | 7/1995 | Larsson-Backström | ...... | 514/549 |
| 5,922,692 A * | 7/1999 | Marino | .......................... | 514/54 |
| 6,022,867 A | 2/2000 | Ito et al. | .......................... | 514/100 |
| 6,265,450 B1 | 7/2001 | Asami et al. | .................. | 514/691 |
| 6,472,209 B1 | 10/2002 | Richelson et al. | ............ | 435/375 |
| 6,552,081 B1 | 4/2003 | Freedman et al. | ............ | 514/560 |
| 2004/0068010 A1 | 4/2004 | Zicker et al. | .................. | 514/560 |
| 2005/0043405 A1* | 2/2005 | Fritsch et al. | ................. | 514/560 |

FOREIGN PATENT DOCUMENTS

| | | | |
|---|---|---|---|
| EP | 0 678 247 | * | 10/1995 |
| EP | 0678247 | * | 10/1995 |
| EP | 0 713 653 A1 | | 5/1996 |
| WO | WO 03/092405 A2 | | 11/2003 |
| WO | WO 2005/018630 A1 | | 3/2005 |
| WO | WO 2005/053710 | * | 6/2005 |

OTHER PUBLICATIONS

Nesbitt et. al. (Veterinary Dermatology (2003) 14:67-74).*
Adam, O., "Dietary fatty acids and immune reactions in synovial tissue," *Europ. J. of Med. Res.*, Germany, 2003, ISSN 0949-2321, 1 page.
Adan, Y., et al., "Effects of docosahexaenoic and eicosapentaenoic acid on lipid metabolism, eicosanoid production, platelet aggregation and atherosclerosis in hypercholesterolemic rats," *Bioscience, Biotechnology, & Biochemistry*, 1999, 63(1), 111-119, 1 page.
Curtis, C.L., et al., "The effect of n-3 (omega-3) polyunsaturated fatty acids on degenerative joint disease," *Agro Food Industry Hi-Tech*, 2003, 14(3), 22-26, 1 page.
de Vizia, B., et al., "Effect of an 8-month treatment with omega-3 fatty acids (eicosapentaenoic and docosahexaenoic) in patients with cystic fibrosis," *J. of Parenteral and Enteral Nutrition*, 2003, 23(1), 52-57, 2 pages.
Dyer, C.A., et al., "Structural features of synthetic peptides of apolipoprotein E that bind the LDL receptor," *J. of Lipid Res.*, 1995, 36, 80-88.
Hansen, R.A., et al., "N-3 fatty acids decrease inflammatory mediators in arthritic dogs," *FASEB J.*, 2003, 17(4-6), Abstract No. 200.3, 2 pages.
Richardson, D.C., et al., "Nutritional management of osteoarthritis," *Osteoarthritis*, 1997, 27(4), 883-911.
Tomobe, Y., et al., "Dietary docosahexaenoic acid suppresses inflammation and immunoresponses in contact hypersensitivity reaction in mice," *Lipids*, 2000, 35(1), 61-69, 1 page.
van Haaster, C.M.C.J., et al., "Formation of prostanoids and hydroxyl fatty acids by stimulated peritoneal mast cells: role of the dietary fat type in rat," *Biochimica et Biophysica Acta*, 1993, 1167, 147-154.
Volker, D.H., et al., "The Eicosapentaenoic to docosahexaenoic acid ratio of diets affects the pathogenesis of arthritis in Lew/SSN rats," *Nutrient Metabolism*, 2000, 559-565.
Alonzi, T., et al., "Interleukin 6 is required fro the development of collagen-induced arthritis," *J. Exp. Med.*, 1998, 187(4), 461-468.
Amin, A.R., et al., "Superinduction of cyclooxygenase-2 activity in human osteoarthritis-affected cartilage," *J. Clin. Invest.*, 1997, 99, 1231-1237.
Anderson, M.A., "Oral chondroprotective agents. Part I. Common compounds." *Compendium*, 1999, 21, 601-609.
Bae, S.C., et al., "Inadequate antioxidant nutrient intake and altered plasma antioxidant status of rheumatoid arthritis patients," *J. Am. Coll. Nutr.*, 2003, 22, 311-315.
Bauer, J.E., et al., "Predictive equations for the quantitation of polyunsaturated fats in dog plasma and neutrophils from dietary fatty acid profiles," *J. Nutr.*, 2002, 132, 1642S-1645S.
Blain, E.J., et al., "Up-regulation of matrix metalloproteinase expression and activation following cyclical compressive loading of articular cartilage in vitro," *Arch Biochem. Biophy.*, 2001, 396, 49-55.
Brooks, P., "Inflammation as an important feature of osteoarthritis," *Bull World Health Org.*, 2003, 81(9), 689-690.
Bui, L.M., et al., "Influence of green lipped mussels (*Perna canaliculus*) in alleviated signs of arthritis in dogs," *Vet. Ther.*, 2001, 2, 101-111.
Cawston, T., "Matrix metalloproteinases and TIMPs: properties and implications for the rheumatic diseases," *Mol. Med. Today*, 1998, 4, 130-137.
Cerhan, J.R., et al., "Antioxidant micronutrients and risk of rheumatoid arthritis in a cohort of older women," *Am. J. Epidemiol*, 2003, 157(4), 345-354.
Chen, J.R., et al., "Comparison of the concentrations of pentosidine in the synovial fluid, serum and urine of patients with rheumatoid arthritis and osteoarthritis," *Rheumatol.*, 1999, 38, 1275-1278.
Clegg, P.D., et al., "Matrix metalloproteinase-2 and -9 are activated in joint disease," *Equine Vet. J.*, 1999, 31, 624-330.
Cleland, J.G., et al., "Omega-6/omega-3 fatty acids and arthritis," *World Rev. Nutr. Diet*, 2003, 92, 152-168.
Coughlan, A.R., et al., "Matrix metalloproteinases 2 and 9 in canine rheumatoid arthritis," *Vet. Rec.*, 1998, 143, 219-223.

(Continued)

*Primary Examiner* — Marcos Sznaidman
(74) *Attorney, Agent, or Firm* — Potter Anderson and Corroon LLP

(57) ABSTRACT

Dietary formulations and methods for treating, preventing or delay onset of osteoarthritis in canines and other animals are disclosed. The formulations are enriched in n-3 fatty acids and limited in n-6 fatty acids.

16 Claims, 10 Drawing Sheets

(56) References Cited

OTHER PUBLICATIONS

Crovetti, R., et al., "The influence of themic effect of food on satiety," *Eur. J. Clin. Nutr.*, 1998, 52, 482-488.
Curtis, C.L., et al., "Pathologic indicators of degradation and inflammation in human osteoarthritic cartilage are abrogated by expose to n-3 fatty acids," *Arthritis Rheum.*, 2002, 46, 1544-1553.
Curtis, C.L., et al., "n-3 fatty acids specifically modulate catabolic factors involved in articular cartilage degradation," *J. Biol. Chem.*, 2000, 275(2), 721-724.
Curtis, C.L., et al., "The effect of n-3 (omega-3) polyunsaturated fatty acids on degenerative joint disease," *Agro Food Industry Hi-Tech*, 2003, 14(3), 122-126.
Deal, C.L., et al., "Nutraceuticals as therapeutic agents in osteoarthritis. The role of glucosamine, chondroitin sulfate and collagen hydrolysate," *Rheum. Dis. Clin. N Am.*, 1999, 25, 379-395.
deHooge, A.S., et al., "Involvement of IL-6, apart from its role in immunity, in mediating a chronic response during experimental arthritis," *Am. J. Pathol.*, 2000, 157, 2081-2091.
Drevon, C.A., et al., "Marine oils and their effects," *Nutr. Rev.*, 1992, 50, 38-45.
Drinda, S., et al., "Identification of the advanced glycation end products $N^\epsilon$—carboxymethyllysine in the synovial tissue of patents with rheumatoid arthritis," *Ann Rheum Dis.*, 2002, 61, 488-492.
Hannah, S.S., et al., "Increased dietary protein spares lean body mass during weight loss in dogs," *J. Vet. Int. Med.*, 1998, 12, 224.
Hansen, R.A., et al., "Long chain n-3 PUFA improved biochemical parameters associated with canine osteoarthritis," *Proc. Am. Oil. Chem. Soc. Meeting*, Cincinnati, May 9-12, 2004, 1 page. (Abstract).
Haynes, M.K., et al., "Phenotypic characterization of inflammatory cells from osteoarthritic synovium and synovial fluids," *Clin. Immunol.*, 2002, 105, 315-325.
Hegemann, N., et al., "Biomarkers of joint tissue metabolism in canine osteoarthritic and arthritic joint disorders," *Osteoarthritis Cartilage*, 2002, 10, 714-721.
Henrotin, Y.E., et al., "The role of reactive oxygen species in homeostasis and degradation of cartilage," *Osteoarthritis Cartilage*, 2003, 11, 747-755.
Jaswal S., et al., "Antioxidant status in rheumatoid arthritis and role of antioxidant therapy," *Clin. Chim. Acta.*, 2003, 338, 123-129.
Jikimoto, T., et al., "Thioredoxin as a biomarker for oxidative stress in patients with rheumatoid arthritis," *Mol. Immunol.*, 2002, 38, 765-772.
Kurz, B., et la., "Dietary vitamins and selenium diminish the development of mechanically induced osteoarthritis and increase the expression of antioxidative enzymes in the knee joint of STR/1N mice," *Osteoarthritis Cartilage*, 2002, 10, 119-126.
Marini, S., et al., "A correlation between knee cartilage degradation observed by arthroscopy and synovial proteinases activities," *Clin. Biochem.*, 2003, 36, 295-304.
Masuhara, K., et al., "Matrix metalloproteinases in patients with osteoarthritis of the hip," *Int. Orthop.*, 2000, 24, 92-96.
Masuhara, K., et al., "Significant increases in serum and plasma concentrations of matrix metalloproteinases 3 and 9 in patients with rapidly destructive osteoarthritis of the hip," *Arthritis Rheum.*, 2002, 46, 2625-2631.
Mazzetti, I., et al., "Differential roles of nitric oxide and oxygen radicals in chondrocytes affected by osteoarthritis and rheumatoid arthritis," *Clin. Sci.*, 2001, 101, 593-599.
McCoy, J.M., et al., "The role of prostaglandin E2 receptors in the pathogenesis of rheumatoid arthritis," *J. Clin. Invest.*, 2002, 110, 651-658.
Miller, C., et al., "Tumor necrosis factor-α levels in adipose tissue of lean and obese cats," *J. Nutr.*, 1998, 128, 2751S-2752S.
Miller, W.H., et al., "Treatment of dogs with hip arthritis with a fatty acid supplement," *Canine Pract.*, 1992, 17, 6-8.
Pan, M.R., et al., "Non-steroidal anti-inflammatory drugs inhibit matrix metalloproteinase-2 expression via repression of transcription in lung cancer cells," *FEBS Letts.*, 2001, 508, 365-368.
Stone, J., et al., "Inadequate calcium, folic acid, vitamine E, zinc, and selenium intake in rheumatoid arthritis patients: results of a dietary survey," *Semin Arthritis Rheum.*, 1998, 27, 180-185.
Tanaka, A., et al., "Expression of matrix metalloproteinase-2 and -9 in synovial fluid of the temporomandibular joint accompanied by anterior disc displacement," *J. Oral Pathol. Med.*, 2001, 30, 59-64.
Tetlow, L.C., et al., "Matrix metalloproteinase and proinflammatory cytokine production by chondrocytes of himan osteoarthritic cartilage," *Arthritis Rheumatism*, 2001, 44, 585-594.
Tiku, M.L., et al., "Evidence linking chondrocyte lipid peroxidation to cartilage matrix protein degradation. Possible role in cartilage aging and the pathogenesis of osteoarthritis," *J. Biol. Chem.*, 2000, 275, 20069-20076.
Waldron, M.K., et al., "Neutrophil leukotriene synthesis and superoxide production are differentially modulated by type and amount of dietary n-3 polyunsaturated fatty acids," *AOCS*, 2000, S118 (Abstract).
Watkins, B.A., et al., "Omega-3 polyunsaturated fatty acids and skeletal health," *Exp. Biol. Med.*, 2001, 226, 485-497.

\* cited by examiner

OSTEOARTHRITIS DIET FORMULATIONS

CROSS-REFERENCE TO RELATED APPLICATIONS

This claims benefit of U.S. Provisional Application No. 60/584,703, filed Jul. 1, 2004, which is incorporated by reference herein in its entirety.

FIELD OF THE INVENTION

The invention relates to methods of treating canines and other animals with osteoarthritis, and specially-formulated foods, supplements and pharmaceuticals to treat, prevent or delay onset of osteoarthritis in canines and other animals, and to maintain healthy joints in animals.

BACKGROUND OF THE INVENTION

Osteoarthritis (OA), also called degenerative joint disease, is the most prevalent joint disorder in humans and animals (Romich, J. A. (1994) *Top. Vet. Med.* 5:16-23; Brooks, P. (2003) *Bull. World Health Org.* 81:689-690). As many as 20% of adult dogs are affected with OA, and suffer pain and disability as a result (Roush et al. (2002) *Vet. Med.* 97:108-112). OA can be defined as a disorder of movable joints, with associated deterioration of articular cartilage; osteophyte formation and bone remodeling; and changes in periarticular tissues. Although the condition is classified as a noninflammatory arthropathy, a low-grade, nonpurulent inflammation is common and several inflammatory components have been strongly associated with OA (Johnston et al. (1997) *Vet. Clin. N. Am. Sm. Anim. Pract.* 27:699-723; Amin et al. (1997) *J. Clin. Invest.* 99:1231-1237; Brooks et al. (2003) Bull. World Health Org. 81:689-690; Haynes et al. (2002) *Clin. Immunol.* 105:315-325). On a cellular and biochemical level, OA is associated with increases in degradative enzymes (especially the matrix metalloproteinases) released from chondrocytes in response to inflammatory cytokines. Inflammatory cytokines, such as interleukin-1β (IL-1), interleukin-6 (IL-6) and tumor necrosis factor alpha (TNFα), as well as other inflammatory mediators, are increased in the synovial fluid of patients with OA.

Matrix metalloproteinases (MMPs), which are variably produced by chondrocytes, leukocytes and fibroblasts, include collagenases, stromelysins, gelatinases, elastase and others. All these enzymes break down cartilage matrix in some manner, and play an important role in physiologic remodeling of cartilage and other connective tissues. In OA, MMPs degrade glycosaminoglycans, including matrix glycoproteins, and collagen. They also reduce hyaluronic acid concentrations in the synovial fluid, leading to less viscous synovial fluid and impairing joint lubrication. Under normal conditions, the degradative processes of MMPs are appropriately balanced through the inhibitory function of tissue inhibitors of metalloproteinases (TIMPs). However, in OA, this balance is disrupted, with a disproportionate increase in MMPs. In addition, inflammatory cytokines, especially IL-1 and TNFα, stimulate the activation and release of MMPs.

Numerous studies, in dogs and other species, have documented increases in active MMPs, reductions in TIMP, or both, in OA. For example, it has been demonstrated that the degree of cartilage degradation in knee OA, as determined by arthroscopy, was strongly related to the activities of MMP-2 and MMP-13, as well as to the reduced inhibitory effect of TIMP-2 on MMP-2. Synovial fluid from dogs with naturally occurring OA has been shown to have higher MMP-2 activity, and dramatic increases in MMP-9 activity, compared to healthy controls (Volk S. W. et al. (2003) *Am. J. Vet. Res.* 64(10):1225-1233). MMP-9 has been correlated with rapidly destructive OA in the hip joint of women undergoing total hip replacement. Similarly, MMP-3 and MMP-9 were shown to be increased in blood, and MMP-1, MMP-3, MMP-9 and TIMP-1 all were shown to be increased in tissue samples from patients with this severe form of OA.

Given their important role in OA, it has been suggested that MMPs could serve not only as a therapeutic target for agents aimed at ameliorating cartilage destruction, but also may serve as useful markers for diagnosing and monitoring the progression of OA. An increase in MMP activity is stimulated by prostaglandins, including prostaglandin $E_2$ ($PGE_2$), which may be inhibited by non-steroidal anti-inflammatory drugs or other compounds that decrease $PGE_2$ production.

The cytokines believed to be of greatest importance in OA include IL-1, IL-6 and TNFα. The cytokines and other inflammatory mediators in OA come from macrophages, lymphocytes, fibroblasts, synoviocytes and chondrocytes. Elevated concentrations of IL-1 and TNFα cause synovial inflammation as well as degradation of cartilage and proteoglycans through activation of MMPs. IL-1 stimulates the release of $PGE_2$ from fibroblasts, which subsequently stimulate pain receptors. In addition, these cytokines stimulate the production of inflammatory free radicals, especially nitric oxide (NO).

The activity of IL-6 in synovial fluid is greatly increased in both dogs and humans suffering from OA. IL-6 can promote anabolic activity in OA through inhibition of MMP activation and promotion of matrix synthesis. On the other hand, IL-6 can stimulate MMP-2, MMP-9 and MMP-13. Thus, this pleiotropic cytokine helps reduce proteoglycan loss in the acute phase of OA, but enhances osteophyte formation in chronic phases. Several studies using IL-6$^{-/-}$ knock-out mice models have shown that IL-6 is critical to the development of arthritic lesions.

Other inflammatory agents involved in the pathogenesis of OA include the eicosanoids $PGE_2$, thromboxane $A_2$ ($TXA_2$) and leukotriene $B_4$ ($LTB_4$), produced from arachidonic acid via cyclooxygenase-2 (COX-2) or 5-lipooxygenase (LOX) enzymes. The activity of these enzymes, and resulting eicosanoids, are increased in OA: osteoarthritic cartilage spontaneously releases 50 times more $PGE_2$ compared to normal cartilage. $LTB_4$ promotes the synthesis and release of IL-1 and TNFα. Further, $LTB_4$ is a potent chemotactic agent and can increase neutrophil-induced damage to local tissues. $TXA_2$ stimulates monocytes to release TNFα and IL-1, which subsequently promote MMP production and joint destruction. $PGE_2$ promotes local inflammation and pain. It can promote osteoclastic bone resorption, increased destruction of Type II collagen and loss of proteoglycans. $PGE_2$ stimulates IL-6 release from fibroblasts, and it also sensitizes chondrocytes to the effects of the free radical NO. Inhibition of the COX-2 enzyme results in a decrease in $PGE_2$, as well as a reduction in IL-6.

There is no known cure for OA, so treatment is focused on controlling pain, improving joint function and slowing the degenerative process within the joint. Therapy usually involves weight management, controlled exercise, and anti-inflammatory and analgesic medications. It may also include nutritional supplements to help reduce inflammatory mediators, promote chondrocyte health and repair, and reduce oxidative damage.

Inhibition of the COX-2 enzyme responsible for $PGE_2$ production is one means of providing relief for OA patients. Another means of reducing $PGE_2$ production is through the use of dietary long chain omega-3 (n-3) polyunsaturated fatty acids (PUFA), which compete with arachidonic acid as substrates for the COX and LOX enzymes. Dietary long chain n-3 PUFA also suppress the pro-inflammatory mediators IL-1, IL-2 and TNF in cartilage tissue (Curtis, C. L. et al. (2000) *J. Biol. Chem.* 275(2):721-724).

Polyunsaturated fatty acids in both the n-6 and n-3 families can have immunomodulatory effects. The primary n-6 fatty acid in canine cell membranes is arachidonic acid (AA; 20:4n-6), which serves as the precursor for the production of $PGE_2$, $TXA_2$ and $LTB_4$, potent inflammatory mediators in OA.

Polyunsaturated fatty acids of the omega-3 (n-3) or omega-6 (n-6 type) are not synthesized de novo in animal tissue and are required for normal cellular function. Thus, they are considered essential. The essential polyunsaturated fatty acids are linoleic acid (LA: 18:2n-6) and α-linolenic acid (ALA; 18:3n-3). When an animal is fed with a source of n-3 or n-6 polyunsaturated fatty acids, including 18:2n-6, 18:3n-3, 20:5n-3, 22:5n-3, and 22:6n-6, there is a corresponding enrichment of n-3 and n-6 highly unsaturated fatty acids (HUFAs), specifically 20:4n-6, 20:5n-3, 22:5n-3, 22:6n-3, into the circulation and in tissue enrichment. Because the precursors of the n-3 and n-6 HUFAs can only be obtained from dietary sources, their relative abundance in tissues is limited by the availability of these precursors in the diet.

If the diet is enriched with long chain n-3 PUFA, specifically eicosapentaenoic acid (EPA; 20:5n-3) and docosahexaenoic acid (DHA; 22:6n-3), part of the AA in cell membranes will be replaced by these long chain n-3 fatty acids. EPA can serve as alternate substrate for the COX-2 and 5-LOX enzymes, resulting in a different and less inflammatory set of compounds, e.g., $PGE_3$, $TXA_3$ and $LTB_5$ instead of $PGE_2$, $TXA_2$ and $LTB_4$.

The majority of clinical studies evaluating long chain n-3 PUFA in arthritis have been in human patients with rheumatoid arthritis. Most of those studies showed positive benefits from long-chain n-3 PUFA supplementation. Patients were able to reduce or discontinue the use of non-steroidal anti-inflammatory drugs (NSAIDs) without experiencing pain or joint stiffness. The beneficial response appeared to be directly linked to the dosage and duration of time receiving the long chain n-3 PUFA supplements. Similar effects have been shown in dogs with OA. Twenty-two dogs with OA of the hip were given a fatty acid supplement marketed for dogs with inflammatory skin conditions (DVM Derm Caps, DVM Pharmaceuticals, Miami, Fla.) (Miller et al. (1992) *Canine Pract.* 17:6-8). When dosed according to the manufacturer's recommendation, 13 of 22 dogs showed noticeable improvement in their arthritic symptoms within two weeks (Miller et al., 1992, supra).

Glucosamine, an amino-sugar, is the principal component of the O-linked and N-linked glycosaminoglycans (GAGs) that form the matrix in connective tissues. Hyaluronan and keratan sulfate are composed, in part, of repeating units of acetyl glucosamine. A decrease in glucosamine synthesis by chondrocytes has been implicated in the decline in matrix GAGs found in OA. Oral supplementation with glucosamine in the management of OA has been evaluated. Essentially all trials evaluating glucosamine have been done with a purified salt, such as glucosamine sulfate or glucosamine hydrochloride. The applicability of these data to glucosamine from natural sources (animal or poultry cartilage) has not been described.

More than 50% of orally administered glucosamine is non-ionized at the physiologic pH of the small intestine and, as a small molecule, is readily absorbed. Most orally administered glucosamine is oxidized, with 70% of the associated radiolabel detected in exhaled $CO_2$. However, approximately 10% is retained in tissue. Glucosamine has a stimulatory effect on chondrocytes, and is incorporated into the proteoglycans and collagen of extracellular matrix.

Several short and long-term, double-blinded, randomized trials evaluating glucosamine supplementation in human patients with OA of the knee were recently reviewed via meta-analysis. These studies documented significant improvement in clinical signs of OA with 1500 mg glucosamine per day. Two studies followed patients for three years and documented that oral glucosamine efficiently inhibited the long-term progression of OA. Similar studies on glucosamine alone in dogs are lacking. However, several in vitro and in vivo canine studies showed a benefit to a combination of glucosamine and chondroitin sulfate.

Oxidative stress plays an important role in both inflammation and tissue destruction in arthritis. Arthritic patients have reduced concentrations of serum vitamins A, E and C and other antioxidants, as well as increased markers of oxidative damage. These anomalies could be reversed with antioxidant supplementation. Several studies support the benefit of supplemental antioxidants for controlling the oxidative damage in OA.

In addition to nutrient modifications that may help address changes associated with OA directly, dogs need appropriately balanced nutrition to support normal maintenance and regeneration. Dietary deficiencies have been reported for antioxidant nutrients, B-vitamins, zinc, calcium, magnesium and selenium. Each of these nutrients plays a role in the normal maintenance of cartilage and other tissues. Therefore, it is important that dogs with OA receive diets that provide complete and balanced nutrition.

In addition to providing a source of amino acids for proteoglycan and collagen synthesis, dietary proteins are important for their role in helping to maintain an optimum body condition. Protein has several physiologic effects that may be beneficial for weight control: protein stimulates metabolism and protein turnover, induces thermogenesis and promotes satiety. During weight loss and subsequent weight maintenance, increased protein intake promotes loss of body fat with retention of lean body mass. These features of protein may be beneficial to help address excess body weight in dogs with OA.

Standard medical care for arthritic dogs includes weight management, controlled exercise, and anti-inflammatory and analgesic medications. There is a need in the art for additional methods of therapy for canines and other animals with osteoarthritis, as well as therapies for humans to reduce the effects of osteoarthritis.

SUMMARY OF THE INVENTION

The invention provides dietary formulations and methods for treating a canines and other animals with osteoarthritis. One aspect of the invention features a dietary formulation comprising long chain n-3 fatty acids, such as a-linolenic acid (ALA), eicosapentaenoic acid (EPA), docosapentaenoic acid (DPA) or docosahexaenoic acid (DHA), in an amount of at least about 0.1-1.5% by weight of the formulation. In certain embodiments, the long chain n-3 fatty acids are present in an amount of at least about 0.2% to 0.6% of the dietary formulation, or at least about 0.3% to 0.4% of the dietary formulation. In certain embodiments the dietary formulation comprises about 0.2-0.6% EPA or DHA.

In some embodiments, the dietary formulation contains n-6 fatty acids in an amount less than about 3% of the dietary formulation. In certain embodiments, the formulation contains less than about 0.125% arachidonic acid. In other embodiments, the formulation contains less than about 1-2% linoleic acid.

In some embodiments, the dietary formulation contains n-3 and n-6 fatty acids in a ratio of at least about 1:2. In certain embodiments, the ratio of n-3 to n-6 fatty acids is at least about 1:1 or at least about 2:1.

The dietary formulation may comprise additional ingredients, independently selected from glucosamine, chondroitin, antioxidants and nonsteroidal anti-inflammatory drugs.

In certain embodiments, the dietary formulation is a pet food or pet treat product for a dog or cat. Such pet food products may be dry (kibble), semi-moist or moist (canned) food products. In other embodiments, the dietary formulation may be a nutritional supplement.

Another aspect of the invention features a method of treating, preventing or delaying onset of arthritis in a mammal, comprising administering to the mammal a dietary formulation of the type described above. In various embodiments, the arthritis is osteoarthritis or rheumatoid arthritis. In certain embodiments of the method, the mammal is a companion animal such as a dog or cat. In other embodiments, the mammal may be a human.

In certain embodiments, the method utilizes a dietary formulation further comprises ingredients to promote weight loss in the mammal. The method may also further comprise subjecting the mammal to caloric restriction to promote weight loss, or providing controlled exercise to the mammal.

Another aspect of the invention features a method of decreasing production of at least one matrix metalloproteinase in synovial fluid of a mammal comprising administering to the mammal a dietary formulation comprising long chain n-3 fatty acids in an amount of at least about 0.1% to 1.5% by weight of the formulation, as described herein. In certain embodiments, the matrix metalloproteinase is MMP-2 or MMP-9.

Another aspect of the invention features a method of decreasing production of inflammatory cytokines in a mammal comprising administering to the mammal a dietary formulation comprising long chain n-3 fatty acids in an amount of at least about 0.1% to 1.5% by weight of the formulation, as described herein. In certain embodiments, the inflammatory cytokine is interleukin-1, interleukin-6 or tissue necrosis factor-α.

Another aspect of the invention features a method of reducing arachidonic acid in the membranes of a mammal in vivo, comprising administering to the mammal a dietary formulation comprising long chain n-3 fatty acids in an amount of at least about 0.1% to 1.5% by weight of the dietary formulation, as described herein.

Other features and advantages of the present invention will become apparent from the following description and appended claims, taken in conjunction with the accompanying drawings.

DETAILED DESCRIPTION OF ILLUSTRATIVE EMBODIMENTS

Figure 1:
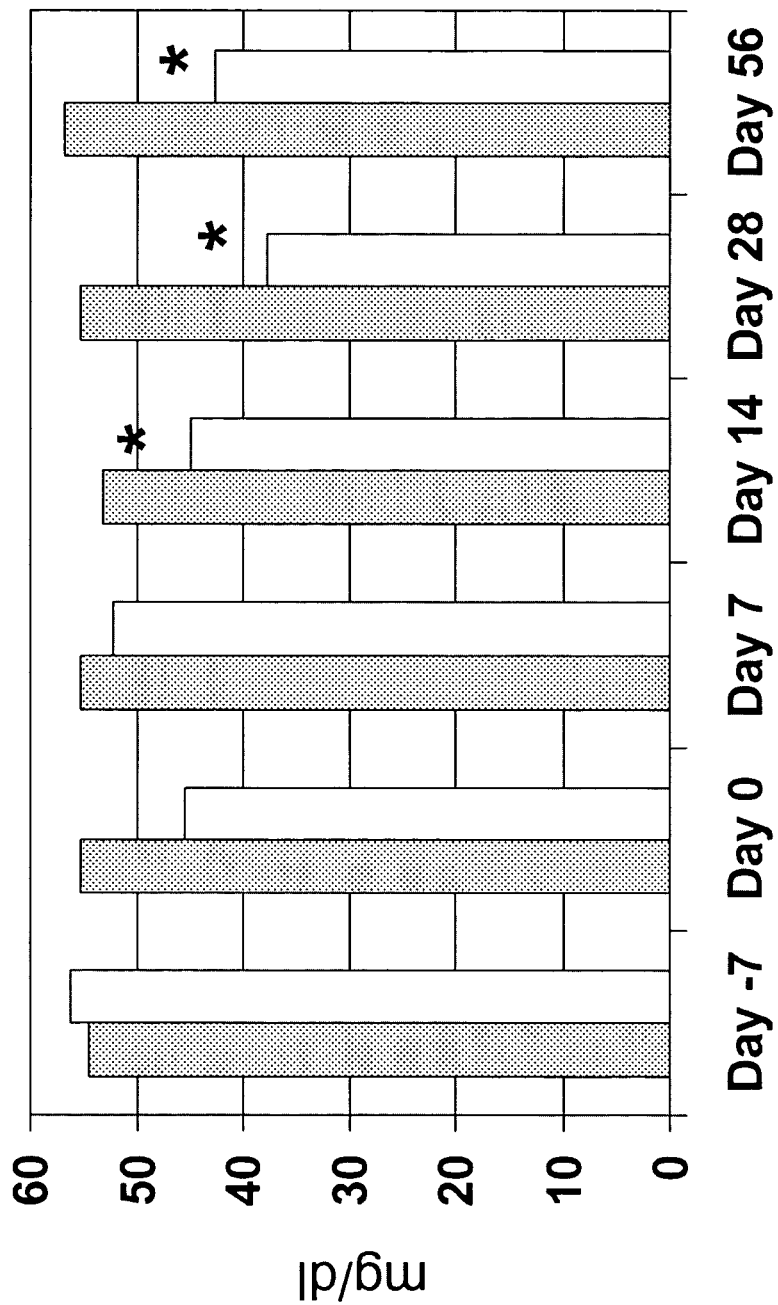
FIG. 1 is a histogram showing concentration of plasma arachidonic acid (mg/dl) in animals provided n-3 fatty acid enriched diets (TRT) or control diets (CTL) before and following corrective surgery to repair ruptured cruciate ligaments. * $p<0.05$. Open bars (TRT); stippled bars (CTL).

The reference works, patents, patent applications, and scientific literature that are referred to herein are hereby incorporated by reference in their entirety to the same extent as if each was specifically and individually indicated to be incorporated by reference. Any conflict between any reference cited herein and the specific teachings of this specification shall be resolved in favor of the latter.

Various definitions are made throughout this document. Most words have the meaning that would be attributed to those words by one skilled in the art. Words specifically defined either below or elsewhere in this document have the meaning provided in the context of the present invention as a whole and as are typically understood by those skilled in the art. Any conflict between an art-understood definition of a word or phrase and a definition of the word or phrase as specifically taught in this specification shall be resolved in favor of the latter. Headings used herein are for convenience and are not to be construed as limiting.

The present invention relates to any animal, preferably a mammal; particularly cats and dogs. In some embodiments, the methods and dietary formulations set forth herein are applicable to humans, as will be appreciated by the person of skill in the art.

As used herein, "treating, preventing or delaying onset" in connection with inflammatory conditions such as arthritis, refers to partially or fully ameliorating the condition or one or more symptoms associated with the condition, completely inhibiting the occurrence of the condition, or retarding the presentation or development of the condition.

The invention provides dietary formulations for canines and other animals rich in n-3 fatty acids. This class of fatty acids, also referred to as omega 3 fatty acids, typically contain 12-26 carbon atoms containing one or more carbon-carbon double bonds. Preferred for use in the present invention are long chain (18 or more carbon atoms) polyunsaturated n-3 fatty acids (LPUFAs). Examples of such n-3 fatty acids include but are not limited to the essential n-3 fatty acid, α-linolenic acid (LNA or ALA), and other n-3 fatty acids, such as eicosapentaenoic acid (EPA), docosapentaenoic acid (DPA) and docosahexaenoic acid (DHA). Dietary sources of n-3 fatty acids include, but are not limited to flax seed, flax oil, walnuts, cold-pressed canola oil, wheat germ, dark green, leafy vegetables, and oily cold-water fish.

As discussed in greater detail below, the formulations preferably contain an amount of long chain n-3 fatty acids that is greater than about half the amount of any long chain n-6 fatty acids present in the formulation. Examples of n-6 fatty acids include the essential n-6 fatty acid linoleic acid (LA) and other n-6 fatty acids, such as arachidonic acid (AA) and γ-linoleic acid (GLA). Dietary sources of n-6 fatty acids include, but are not limited to soy oil, sunflower seeds, safflower seeds, pumpkin seeds, sesame seeds, tahini, corn oil, peanuts and most nuts. In general, the amounts of n-6 fatty acids are limited. For example, the amount of arachidonic acid in the formulation is less than about 0.125% by weight. Further, the linoleic acid content of the formulation is in the range of about 1-2% by weight.

The formulations of the invention contain an effective amounts of long chain n-3 fatty acids. As used herein "effective amount" refers to an amount of long chain n-3 fatty acids that ameliorates at least one sign or symptom of osteoarthritis, including, but not limited to pain, lameness, cartilage loss, joint swelling, crepitus, difficulty in posturing to defecate or urinate, stiffness, gait abnormality, joint laxity, joint effusion, increased synovial fluid volume, and the like.

In some embodiments, the formulation contains long chain n-3 fatty acids in an amount to deliver about at least about 20 mg/kg bodyweight/day to the animal. In other embodiments, the formulation contains long chain n-3 fatty acids in an amount to deliver at least about 30 mg/kg/day to the animal. In other embodiments, the formulation contains long chain n-3 fatty acids in an amount to deliver at least about 40 mg/kg/day to the animal. In other embodiments, the formulation contains long chain n-3 fatty acids in an amount to deliver at least about 50 mg/kg/day to the animal. In other embodiments, the formulation contains long chain n-3 fatty acids in an amount to deliver at least about 60 mg/kg/day to the animal. In other embodiments, the formulation contains long chain n-3 fatty acids in an amount to deliver at least about 70 mg/kg/day to the animal. In other embodiments, the formulation contains long chain n-3 fatty acids in an amount to deliver at least about 80 mg/kg/day to the animal. In other embodiments, the formulation contains long chain n-3 fatty acids in an amount to deliver at least about 90 mg/kg/day to the animal. In other embodiments, the formulation contains long chain n-3 fatty acids in an amount to deliver at least about 100 mg/kg/day to the animal. In other embodiments, the formulation contains long chain n-3 fatty acids in an amount to deliver at least about 110 mg/kg/day to the animal. In other embodiments, the formulation contains long chain n-3 fatty acids in an amount to deliver at least about 120 mg/kg/day to the animal. In some embodiments of the invention the long chain n-3 fatty acid is one or more n-3 fatty acids selected from α-linolenic acid (ALA), eicosapentaenoic acid (EPA), docosapentaenoic acid (DPA) and docosahexaenoic acid (DHA).

The amount of long chain n-3 fatty acids as a percentage of the dietary formula is in the range of about 0.1-1.5% of the dietary formulation on a dry matter basis, though a greater percentage can be supplied. In various embodiments, the amount is about 0.2%, 0.3%, 0.4%, 0.5%, 0.6%, 0.7%, 0.8%, 0.9%, 1.0%, 1.1%, 1.2%, 1.3%, 1.4% or 1.5% of the dietary formulation on a dry matter basis. In some embodiments of the invention, the long chain n-3 fatty acid is eicosapentaenoic acid (EPA). In some embodiments, the long chain n-3 fatty acid is docosapentaenoic acid (DPA). In other embodiments, the long chain n-3 fatty acid is docosahexaenoic acid (DHA). In still other embodiments, the long chain n-3 fatty acid is α-linolenic acid (ALA). In other embodiments, the dietary formulation contains a mixture of two or more of these n-3 fatty acids.

Average diets may contain a ratio of about 1:10 n-3:n-6 fatty acids. The present formulations limit n-6 fatty acids (particularly AA and LA) to achieve ratios of n-3:n-6 that favor a higher proportion of n-3 fatty acids than an average diet. In some embodiments, the ratio of n-3:n-6 is greater than about 1:9, 1:8, 1:7 or 1:6. In other embodiments, the ratio of n-3:n-6 is greater than about 1:5, 1.4 or 1:3. In another embodiment, the ratio of n-3:n-6 is greater than about 1:2. In other embodiments, the ratio of fatty acids is such that there is an equal or greater proportion of n-3 fatty acids than n-6 fatty acids. For example, the ratio of n-3:n-6 may be about 1:1 to about 15:1. In some embodiments, the ratio is about 2:1 to about 3:1, but can be greater, e.g., 4:1, 5:1, 6:1, 7:1, 8:1, 9:1, 10:1, 11:1, 12:1, 13:1 or 14:1.

Figure 10:
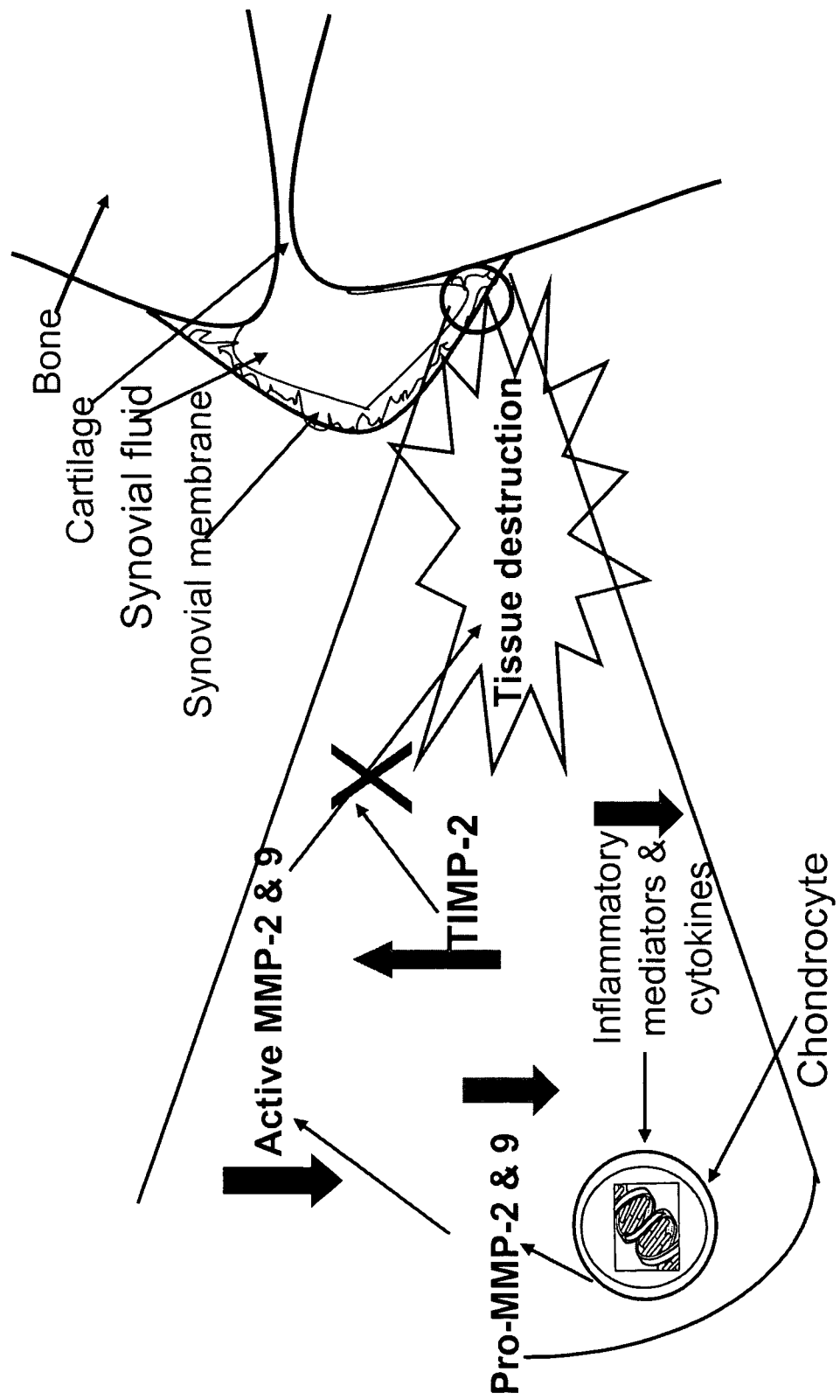
FIG. 10 is a diagram illustrating mechanisms by which n-3 fatty acids may affect joint destruction.

While not wishing to be bound by any particular theory of operability, it is believed that the long chain n-3 fatty acids in the formula, when consumed by the animal, replace arachidonic acid in the membranes of the cells and will be used for the production of anti-inflammatory eicosanoids, driving production of such compounds as prostaglandin $E_3$ ($PGE_3$), thromboxane $A_3$ ($TXA_3$) and leukotriene $B_5$ ($LTB_5$), rather than $PGE_2$, $TXA_2$ and $LTB_4$. The reduction of $PGE_2$ leads to a decrease in pro-MMP-2 and pro-MMP-9, thereby lessening the proteolytic activation of these metalloproteinases, resulting in reduction of inflammation and pain in the joints. In addition, it is believed that the increase in long chain n-3 fatty acids contributes to an increase in tissue inhibitor of metalloproteinases-2 (TIMP-2). which blocks the activation of MMP-2 and MMP-9 by saturating binding sites of other MMPs (such as membrane-type-1 matrix metalloproteinase) that are believed necessary for the first activation step of MMP-2 and MMP-9. FIG. 10 diagrammatically illustrates some of these mechanisms.

Indeed, it has been demonstrated in accordance with the present invention that a dietary formulation enriched in n-3 fatty acids promotes an increase in TIMP-1 and a decrease in two matrix metalloproteinases involved in the breakdown of gelatinase: MMP-2 (Gelatinase-A) and MMP-9 (Gelatinase B) (see Example 2, referring to FIGS. 7, 8 and 9). The formulations of the invention are expected to find practical utility in reducing levels of these and other matrix metalloproteinases, including, but not limited to: (1) collagenases such as interstitial collagenase (MMP-1), neutrophil collagenase (MMP-8) and collagenase-3 (MMP-13); (2) stromelysins such as stromelysin-1 (MMP-3), stromelysin-2 (MMP-10) and matrilysin (MMP-7); and (3) membrane-type MMPs such as MMP-14 and MT1-MMP.

The formula of the invention may also contain additional factors to support joint health such as, but not limited to, glucosamine and chondroitin sulfate.

In some embodiments glucosamine is provided in an amount of 500-1000 ppm of food. In other embodiments, glucosamine is provided in an amount of at least about 1000-1500 ppm. In other embodiments, glucosamine is provided in an amount of at least about 1500-2000 ppm or more, provided no untoward effect results from administration of glucosamine.

In some embodiments chondroitin sulfate is provided in an amount of to deliver about 100-300 mg/day. In other embodiments, chondroitin sulfate is provided in an amount to deliver at least about 300-500 mg/day. In other embodiments, chondroitin sulfate is provided in an amount to deliver at least about 500-700 mg/day or more, provided no untoward effect results from administration of chondroitin sulfate.

The formulation may also include antioxidants, including, but not limited to vitamin A, vitamin C, vitamin E, riboflavin, selenium, and pyridoxine.

In some embodiments selenium is provided in an amount of 0.5-0.7 mg/kg of food. In other embodiments, selenium is provided in an amount of at least about 0.7-0.9 mg/kg. In other embodiments, selenium is provided in an amount of at least about 0.9-1.1 mg/kg or more, provided no untoward effect results from administration of selenium.

In some embodiments, vitamin A is provided in an amount of at least about 20-30 IU/g of food. In other embodiments, vitamin A is provided in an amount of at least about 30-40 IU/g of food. In other embodiments, vitamin A is provided in an amount of at least about 40-50 IU/g of food or more, provided no untoward effect results from administration of vitamin A.

In some embodiments, vitamin E is provided in an amount of at least about 0.5-1 IU/g of food. In other embodiments, vitamin E is provided in an amount of at least about 1-1.5 IU/g of food. In other embodiments, vitamin E is provided in an amount of at least about 1.5-2.5 IU/g of food or more, provided no untoward effect results from administration of vitamin E.

In some embodiments, vitamin C is provided in an amount of at least about 50-150 ppm of food. In other embodiments, vitamin C is provided in an amount of at least about 150-250 ppm. In other embodiments, vitamin C is provided in an amount of at least about 250-350 ppm or more, provided no untoward effect results from administration of vitamin C.

In some embodiments, riboflavin is provided in an amount of at least about 5-15 mg/kg of food. In other embodiments, riboflavin is provided in an amount of at least about 15-25 mg/kg. In other embodiments, riboflavin is provided in an amount of at least about 25-35 mg/kg or more, provided no untoward effect results from administration of riboflavin.

In some embodiments, pyridoxine is provided in an amount of at least about 5-15 mg/kg of food. In other embodiments, pyridoxine is provided in an amount of at least about 15-25 mg/kg. In other embodiments, pyridoxine is provided in an amount of at least about 25-35 mg/kg or more, provided no untoward effect results from administration of pyridoxine.

The formulation may be adjusted to a dietetic formulation to allow animals to lose weight in addition to providing the beneficial effects on osteoarthritis. Proper weight management of animals can promote an enhanced palliative effect in addition to the direct therapeutic effect on joints.

It may be desirable to adjust the formulation for specific needs of the animal, taking into account parameters such as, but not limited to, breed, age, size, weight, and general health status, such as the degree or stage of osteoarthritis, rheumatoid arthritis or other diseases causing an inflammatory response in the animal. Methods for calculating the enrichment of n-3 and n-6 fatty acids in membranes and tissues are known in the art and can be used to adjust for levels of the n-3 and n-6 fatty acids in the diet. For example, such calculations are described in Bauer, J. E. et al. (2002) *J. Nutr.* 132:1642S-1645S and PCT Publication No. WO 03/092405.

The dietary formulation of the invention may be in the form of dry food, soft/moist food or canned food. The protein content of dry food is generally in the range of about 15-30% by weight. The overall fat content of dry food is generally in the range of about 5-20% by weight. The carbohydrate content of dry food is in the range of about 30-60% by weight. The moisture content of dry food is generally less than about 15% by weight. The content of protein, carbohydrate and fat may be adjusted to suit the special needs of different breeds of canines as would be well-known in the art.

The protein content of soft-moist food is generally in the range of about 10-30% by weight. The overall fat content of soft-moist food is generally in the range of about 2-15% by weight. The carbohydrate content of soft-moist food is in the range of about 20-40% by weight. The moisture content of a soft-moist food is generally less than about 20-50% by weight. The content of protein, carbohydrate and fat may be adjusted to suit the special needs of different breeds of canines as would be well-known in the art.

The protein content of canned food is generally in the range of about 5-20% by weight. The overall fat content of canned food is generally in the range of about 1-20% by weight. The carbohydrate content of canned food is in the range of about 15-40% by weight. The moisture content of canned food is generally less than about 80% by weight. The content of protein, carbohydrate and fat may be adjusted to suit the special needs of different breeds of canines as would be well-known in the art.

The dietary formulation of the invention may be also be in the form of a nutritional supplement which may be administered admixed with food or water, or provided separately as a pharmaceutical dosage form. Supplements and dosage forms include, but are not limited to, tablets (including pills, chewable tablets, quick dissolve tablets, multi-layer tablets, bi-layer tablets and the like), powders, elixirs, liquids, solutions, suspensions, emulsions, capsules, caplets, lozenges, chewable lozenges, beads, powders, granules, particles, gels, pastes, dissolvable films, microparticles, dispersible granules, health bars, animal treats, and combinations thereof. The preparation of the above dosage forms are well known to persons of ordinary skill in the art.

The invention also provides methods of treating osteoarthritis in canines by feeding canines dietary formulations of the invention to alleviate the symptoms of osteoarthritis. The amount of the nutrients in the dietary formulations may be adjusted according to the specialized needs of the breed of canine and the degree or stage of osteoarthritis experienced by the animal. A veterinarian will be able to provide guidance as to dietary formulations to be administered to the animal as well as adjusting other parameters of the diet (e.g., to provide for weight management) and may also provide guidance as to the type and duration of other therapy (e.g., pain management, exercise, and the like).

In general, canines in need of weight management as well as treatment for osteoarthritis will be fed a diet with reduced calories to promote weight loss while maintaining an increased amount of long chain n-3 fatty acids to promote alleviation of at least one symptom of osteoarthritis. The dietary formulation may also include other ingredients as detailed above, such as antioxidants, non-steroidal anti-inflammatory drugs, glucosamine, and chondroitin sulfate.

The invention also provides methods of treating healthy animals such that onset of OA may be delayed or prevented, and to support joint health. Thus, the dietary formulations and/or nutritional supplements of the invention may be provided to animals, such as canines, as a prophylactic measure to prevent or delay the onset of OA and to maintain healthy joints. The formulations, supplements or pharmaceuticals contain long chain n-3 fatty acids in an amount of at least about 0.1-1.5% of formulation on a dry matter basis, and the formulations may also include n-6 fatty acids in amounts described herein, as well as antioxidants, glucosamine, chondroitin and/or NSAIDs. The amount of the nutrients in the dietary formulations may be adjusted according to the specialized needs of the breed of canine, for example, and the age of the animal, in accordance with standard procedures.

The methods and dietary formulations provided herein to treat and prevent osteoarthritis may also be used to treat or prevent other inflammatory conditions. In particular, the formulations and methods are expected to be advantageous for the treatment of rheumatoid arthritis as well, in view of the inflammatory nature of that condition.

The invention also provides a method of decreasing arachidonic acid in the membranes of cells of mammals, particularly canines comprising administering a dietary formulation of the invention to the mammal. The amount of long chain n-3 fatty acid in the dietary formulation will be sufficient to replace arachidonic acid in the membranes of cells of the canines. In general, the amount of long chain n-3 fatty acids is about 0.1-1.5% of the dietary formulation on a dry matter basis.

The invention also provides method of reducing the effects of osteoarthritis in a mammal comprising administering a dietary formulation comprising an increased amount of long chain n-3 fatty acid. In some embodiments, the long chain n-3 fatty acid is in an amount of at least about 0.1-1.5% of the dietary formulation on a dry matter basis. In some embodiments, the amount is about 0.3% of the dietary formulation on a dry matter basis. In some embodiments, the amount is about 0.4% of the dietary formulation on a dry matter basis. In some embodiments, the amount is about 0.5% of the dietary formulation on a dry matter basis. In some embodiments, the dietary formulation is for mammals, particularly canines. In other embodiments, the dietary formulation is for humans.

In some embodiments, the dietary formulation for humans is in the form of a nutrition supplement, as is known in the art.

The invention further provides methods for decreasing production of matrix metalloproteinase in canines and other mammals by administering the dietary formulation of the invention. The matrix metalloproteinases include, but are not limited to MMP-2 and MMP-9. Generally, the amount of long chain n-3 fatty acids is in the range of about 0.1 to 1.5% of the formulation on a dry matter basis. The amount of arachidonic acid in the formulation is limited in some embodiments to be less than 0.125%. In other embodiments, the amount of linoleic acid is limited to no more than 1-2% of the dietary formulation. The formulation may also be supplemented with antioxidants, glucosamine and at least one NSAID.

The invention also provides a method of decreasing production of inflammatory cytokines in canines and other mammals by administering a dietary formulation of the invention. The inflammatory cytokines include, but are not limited to IL-1, IL-6 and TNFα. Generally, the amount of long chain n-3 fatty acids is in the range of about 0.1 to 1.5% of the formulation. The amount of arachidonic acid in the formulation is limited in some embodiments to be less than 0.125%. In other embodiments, the amount of linoleic acid is limited to no more than 1-2% of the dietary formulation. The formulation may also be supplemented with antioxidants, glucosamine and at least one NSAID. The dietary formulations may also be used to decrease production of matrix metalloproteinase and/or decrease production of inflammatory cytokines.

The following examples are provided to describe the invention in greater detail. They are intended to illustrate, not to limit, the invention.

Example 1

Experimental Design

This example sets forth a protocol for determining the effect of enriched n-3 fatty acid diets on biochemical parameters associated with OA in canines. A double blind, randomized, and placebo controlled design was utilized.

Twenty four dogs with degenerative osteoarthritis resulting in clinically confirmed acute anterior cruciate ligament (ACL) injury (rupture of the anterior cruciate ligament) were used in the study and randomly allocated to either the treatment diet or the control diet (n=12). Dogs were stratified by degree of OA and ligament injury. Dogs were given routine physical examinations by the surgical clinicians and radiographs were taken prior to the study.

The dogs were randomly divided into two groups of twelve dogs each:

Group 1: n-3 LC PUFA supplement (3.5% added fish oil)

Group 2 (control): containing no long chain n-3 fatty acids, but contained tallow as the added fat source.

Dogs were fed the supplements for a duration of 63 days (7 days before the corrective surgery and 56 days after the corrective surgery).

Synovial fluid and serum for TIMP-2, $PGE_2$, and MMP analysis were obtained by needle and syringe via sterile arthrocentesis and venipuncture, respectively, at the following time points: day −7, day 0, day 7, day 14, day 28, and day 56. Synovial fluid was obtained from the affected (ACL ruptured) and contralateral joints of all dogs.

Gas Chromatography, utilizing an HP 5890 gas chromatograph, was performed to evaluate serum fatty acids and to measure N-3 LC PUFA in serum of the subjects Analysis of the pro- and active form of MMP-2 and MMP-9 in all serum and synovial samples was conducted by electrophoresis using gelatin imbedded gels. Gel analyses used NOVEX Zymogram (San Diego, Calif.) gels, buffers, stains, and equipment. Zymography was run as directed by standardized NOVEX instructions. Gels were scanned on a densitometer (Molecular Dynamics, Sunnyvale, Calif.). Each sample band was compared and quantified against the standards run on each gel.

Serum bicyclo-PGE$_2$, the stable metabolite of PGE$_2$, analysis was conducted using commercial available enzyme linked immunosorbant assay (ELISA) kits available from Caymen (Ann Arbor, Mich.).

Example 2

Figure 2:
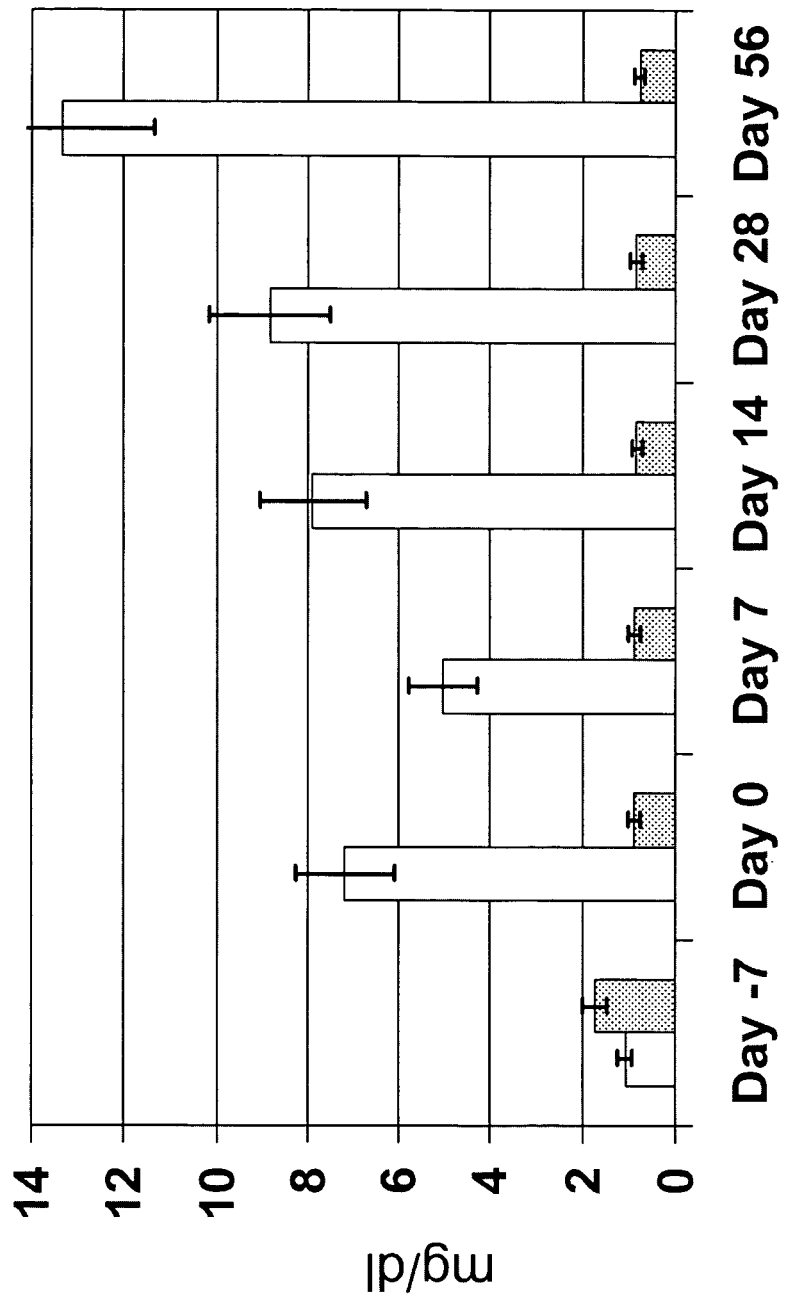
FIG. 2 is a histogram showing concentration of plasma eicosopentaenoic acid (mg/dl) in animals provided n-3 fatty acid enriched diets (TRT) or control diets (CTL) before and following corrective surgery to repair ruptured cruciate ligaments. * $p<0.05$ on all days except day-7. Open bars (TRT); stippled bars (CTL).
Figure 3:
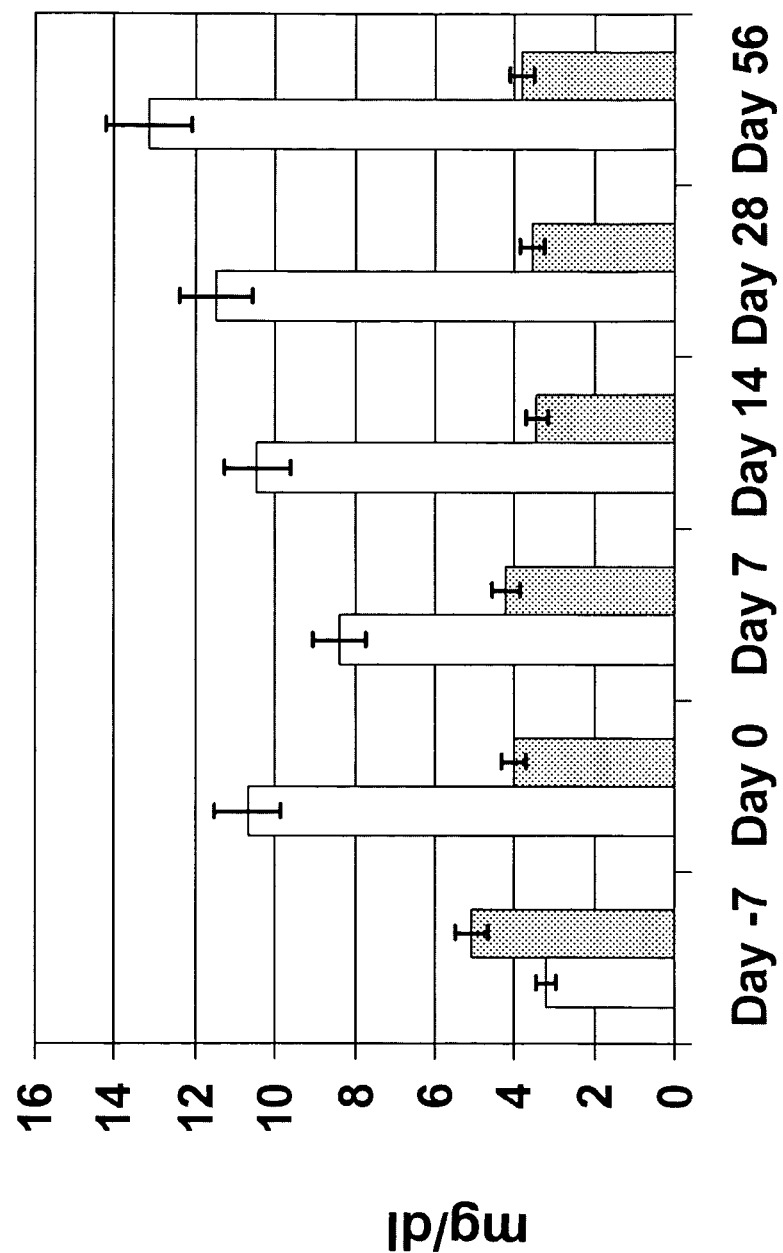
FIG. 3 is a histogram showing concentration of plasma docosahexaenoic acid (mg/dl) in animals provided n-3 fatty acid enriched diets (TRT) or control diets (CTL) before and following corrective surgery to repair ruptured cruciate ligaments. * $p<0.05$ on all days except day-7. Open bars (TRT); stippled bars (CTL).
Figure 6:
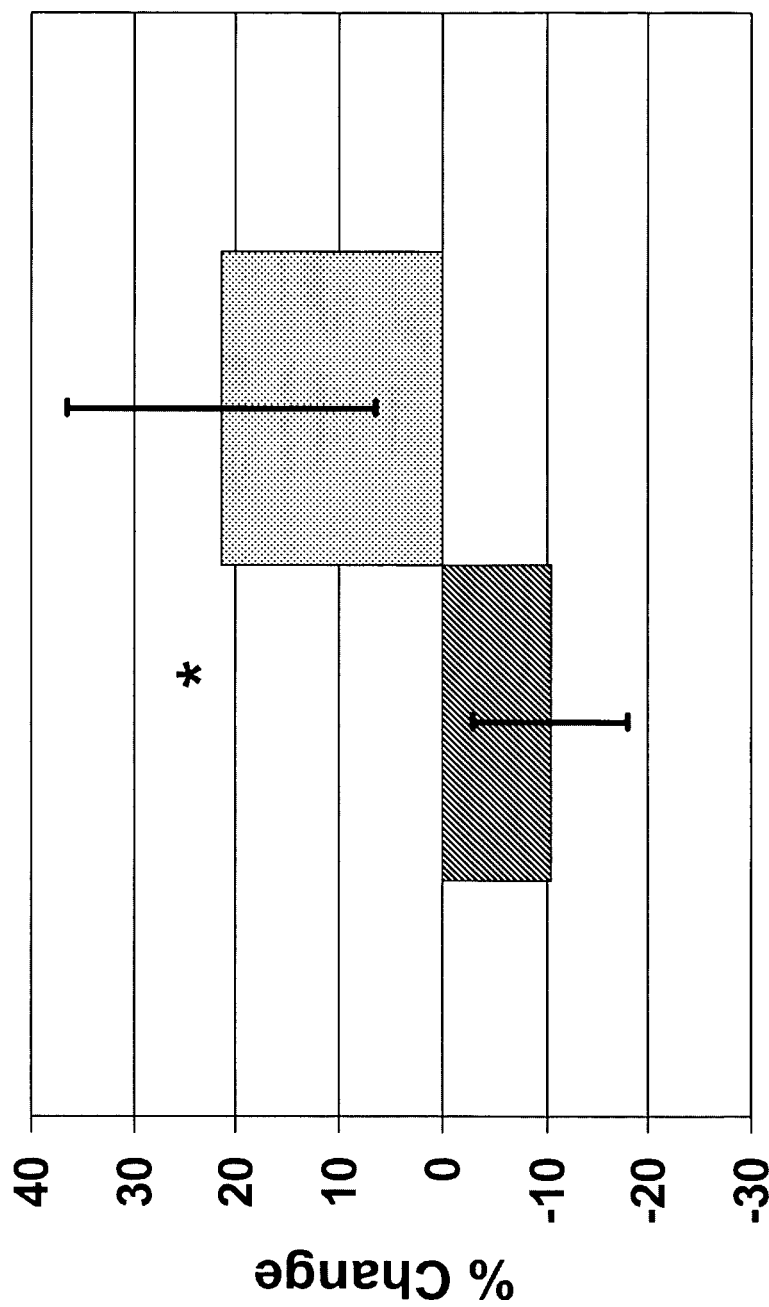
FIG. 6 is a histogram showing the percent change in levels of plasma bicyclo $PGE_2$ in animals provided n-3 fatty acid enriched diets (TRT) or control diets (CTL) before and following corrective surgery to repair ruptured cruciate ligaments. Percent change was measured as a change from initiation to the end of the study. * $p<0.05$. Hatched bars (TRT); stippled bars (CTL).

Effect of Enriched n-3 Fatty Acid Diets on Biochemical Parameters Associated with Canine Osteoarthritis The following results were obtained utilizing the protocol and evaluation procedures set forth in the previous example. First, amounts of AA, EPA and DHA in plasma was measured. Referring now to the figures, FIG. 1 shows that plasma AA was reduced in animals provided n-3 fatty acid-enriched diets, as compared to animals fed control diets. FIGS. 2 and 3 respectively show that plasma EPA and DHA were increased in animals fed the n-3 fatty acid-enriched diets, as compared to animals fed control diets. Additionally, as illustrated in FIG. 6, plasma bicyclo PGE$_2$ decreased by about 10% (from entry to completion of the protocol) in animals fed the n-3 fatty acid enriched diet, but increased by more than 20% in animals fed the control diet.

Figure 4:
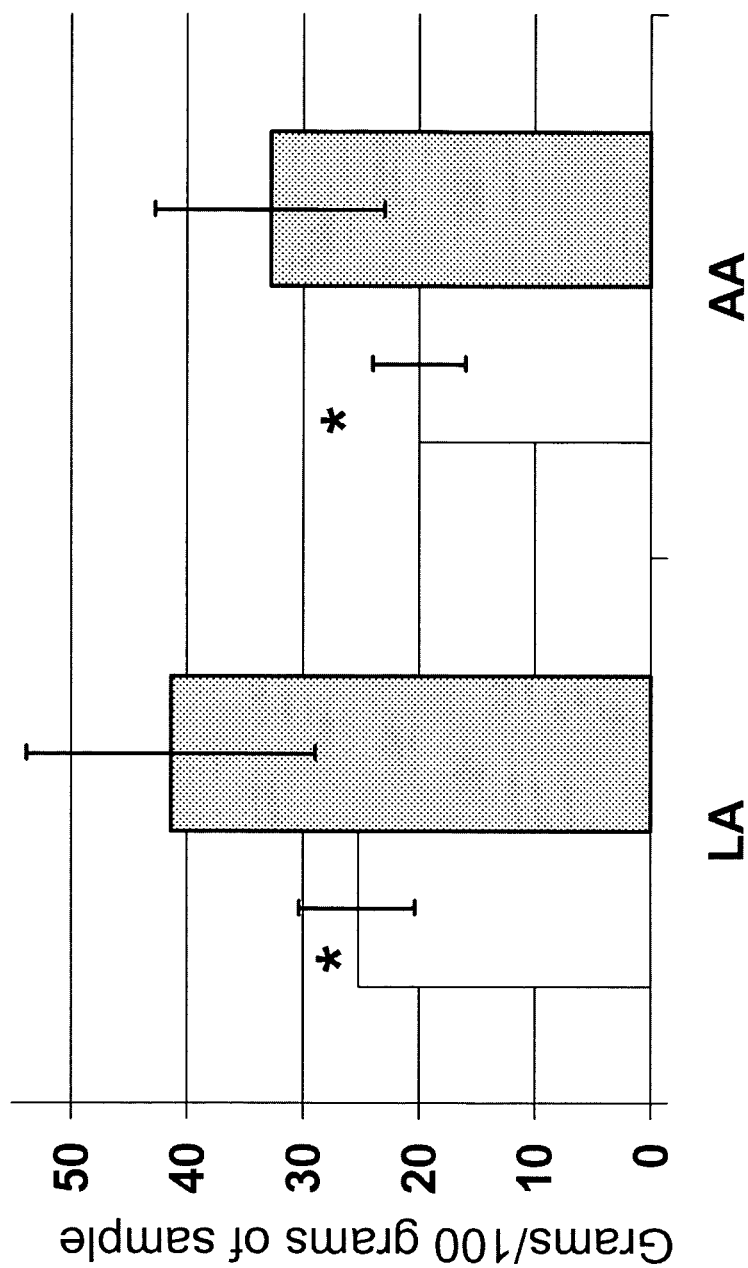
FIG. 4 is a histogram showing amounts of synovial fluid n-6 fatty acids (AA—arachidonic acid; LA—linolenic acid) (g/100 g sample) in animals provided n-3 fatty acid enriched diets (TRT) or control diets (CTL) before and following corrective surgery to repair ruptured cruciate ligaments. Samples were taken on day 28 following surgery. * $p<0.005$. Open bars (TRT); stippled bars (CTL).
Figure 5:
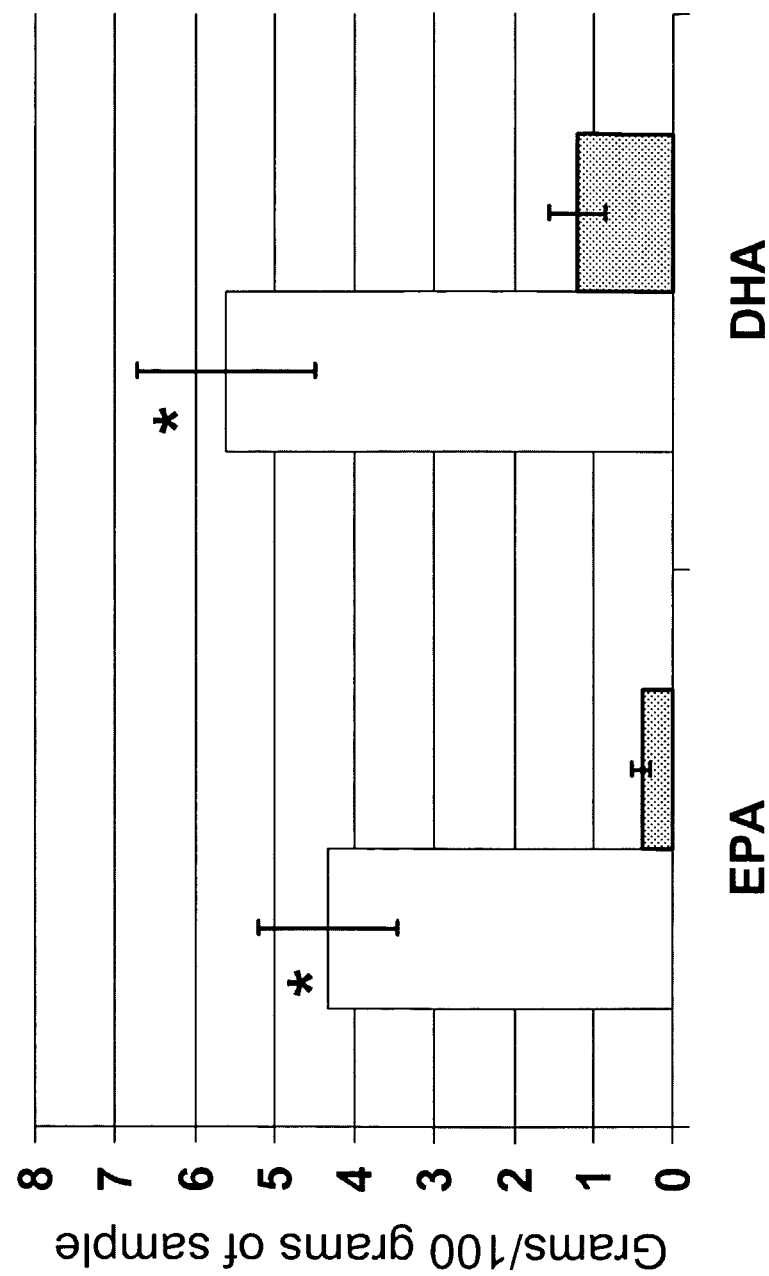
FIG. 5 is a histogram showing amounts of synovial fluid n-3 fatty acids (EPA—eicosopentaenoic acid; DHA—docosahexaenoic acid) (g/100 g sample) in animals provided n-3 fatty acid enriched diets (TRT) or control diets (CTL) before and following corrective surgery to repair ruptured cruciate ligaments. Samples were taken on day 28 following surgery. * $p<0.005$. Open bars (TRT); stippled bars (CTL).
Figure 7:
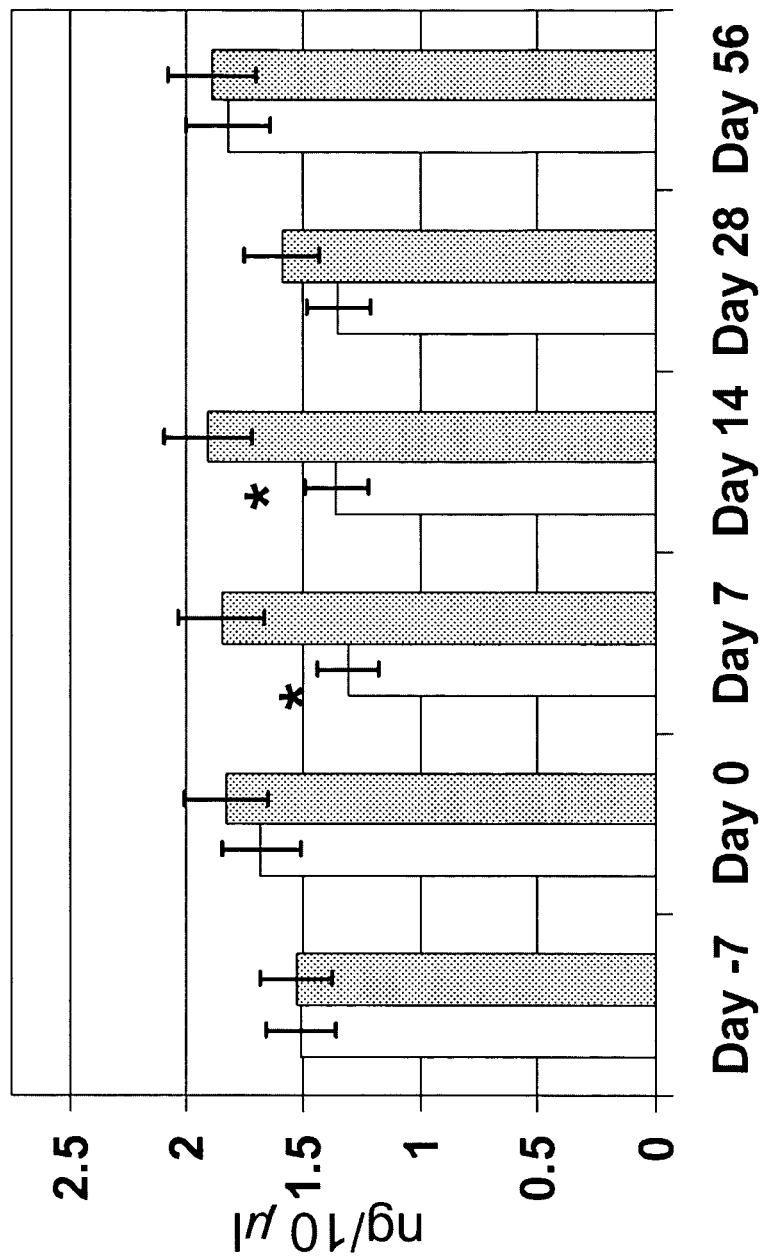
FIG. 7 is a histogram showing concentration of pro-MMP-2 and active MMP-2 (ng/10 µl) in the synovial fluid of non-surgical joints of animals provided n-3 fatty acid enriched diets (TRT) or control diets (CTL) before and following corrective surgery to repair ruptured cruciate ligaments. * $p<0.05$ due to diet. Open bars (TRT); stippled bars (CTL).
Figure 8:
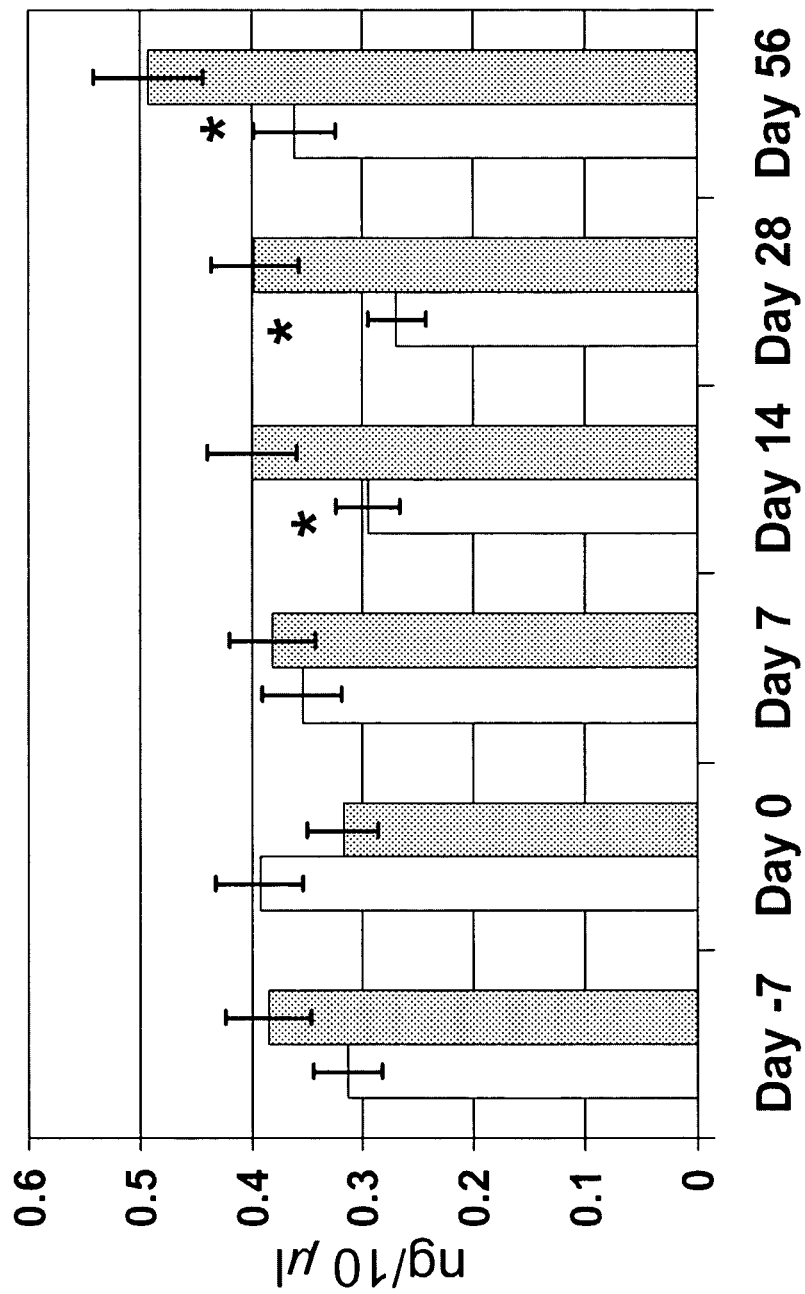
FIG. 8 is a histogram showing concentration of pro-MMP-9 and active MMP-9 (ng/10 µl) in synovial fluid of non-surgical joints of animals provided n-3 fatty acid enriched diets (TRT) or control diets (CTL) before and following corrective surgery to repair ruptured cruciate ligaments. * $p<0.05$ due to diet. Open bars (TRT); stippled bars (CTL).
Figure 9:
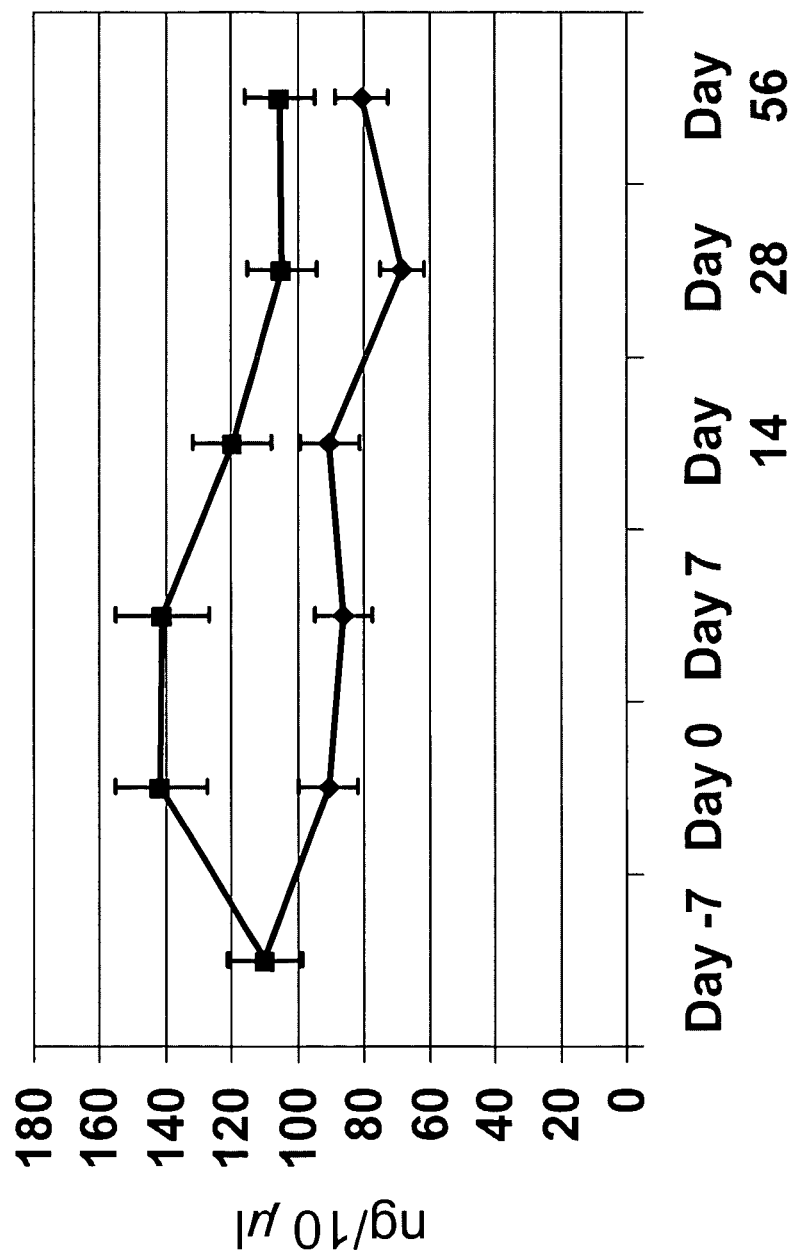
FIG. 9 is a graph showing a time course of concentration of TIMP-2 in synovial fluid (ng/10 µl) of animals provided n-3 fatty acid enriched diets (TRT -■- ) or control diets (CTL -♦-) before and following corrective surgery to repair ruptured cruciate ligaments. * $p<0.05$. Open bars (TRT); stippled bars (CTL).

The fatty acid composition of synovial fluid was also examined. As illustrated in FIGS. 4 and 5, respectively, animals fed an n-3 fatty acid-enriched diet before and after surgery exhibited a decrease in synovial fluid n-6 fatty acids and an increase in synovial fluid n-3 fatty acids, as compared with animals fed a control diet. Furthermore, as shown in FIGS. 7 and 8, pro- and active MMP-2 and MMP-9 were decreased in the synovial fluid of animals fed the n-3 fatty acid-enriched diets, as compared with that of animals fed the control diet. As shown in FIG. 9, TIMP-2 was increased in the synovial fluid of animals fed the n-3 fatty acid-enriched diets, as compared with that of animals fed the control diet.

The results described hereinabove demonstrate that dietary enrichment of n-3 fatty acids improves several physiological and biochemical parameters associated with canine osteoarthritis.

Example 3

Exemplary Dietary Formulation

An exemplary, non-limiting dietary formulation of the invention is as follows:

| Moisture | 9.1% |
|---|---|
| Protein | 27.8% |
| Fat | 12.9% |
| Ash | 8.02% |
| Carbohydrate (by subtraction) | 42.20% |

| Fatty Acid Composition: | Percent of fat |
|---|---|
| 14:0 | 3.13 |
| 14:1 | 0.22 |
| 15:0 | 0.35 |
| 16:0 | 20.9 |
| 16:1 | 5.63 |
| 17:0 | 0.6 |
| 18:0 | 8.08 |
| 18:1n-9 | 29.8 |
| 18:2n-6 | 11.8 |
| 18:3n-6 | 0.18 |
| 20:0 | 0.2 |
| 18:3n-3 | 1.08 |
| 20:2n-6 | 0.25 |
| 20:3n-6 | 0.32 |
| 20:4n-6 | 0.66 |
| 20:5n-3 | 3.09 |
| 22:5n-3 | 0.67 |
| 22:6n-3 | 2.66 |
| Unknowns | 4.66 |

| Fatty Acid Composition: | Percent of formulation |
|---|---|
| EPA | 0.39861% |
| Arachidonic acid | <0.125% |
| Linoleic acid | 1–2% |

Moisture 9.1%
Protein 27.8%
Fat 12.9%
Ash 8.02%
Carbohydrate 42.20% (by subtraction)
Fatty Acid Composition: Percent of fat
14:0 3.13
14:1 0.22
15:0 0.35
16:0 20.9
16:1 5.63
17:0 0.6
18:0 8.08
18:1 n-9 29.8
18:2n-6 11.8
18:3n-6 0.18
20:0 0.2
18:3n-3 1.08
20:2n-6 0.25
20:3n-6 0.32
20:4n-6 0.66
20:5n-3 3.09
22:5n-3 0.67
22:6n-3 2.66
Unknowns 4.66
Fatty Acid Composition: Percent of formulation
EPA 0.39861%
Arachidonic acid <0.125%
Linoleic acid 1-2%

The present invention is not limited to the embodiments described and exemplified above, but is capable of variation and modification within the scope of the appended claims.

What is claimed:

1. A dietary formulation comprising about 0.1 to 1.5% long chain n-3 fatty acids on a dry weight basis, wherein the dietary formulation is a ready-to-eat pet food or pet treat having a moisture content of less than 80% by weight, wherein the long chain n-3 fatty acids are present in an amount that is at least about twice any amount of long chain n-6 fatty acids present in the formulation.

2. The dietary formulation of claim 1, wherein the long chain n-3 fatty acids comprise at least one of α linolenic acid, eicosapentaenoic acid, docosapentaenoic acid or docosahexaenoic acid.

3. The dietary formulation of claim 1, wherein the long chain n-3 fatty acids are present in an amount of from about 0.2% to 0.6% of the dietary formulation.

4. The dietary formulation of claim 3, wherein the long chain n-3 fatty acids are present in an amount of from about 0.3% to 0.4% of the dietary formulation.

5. The dietary formulation of claim 2, comprising about 0.2-0.6% eicosapentaenoic acid.

6. The dietary formulation of claim 2, comprising about 0.2-0.6% docosahexaenoic acid.

7. The dietary formulation of claim 1, which contains arachidonic acid in an amount less than about 0.125% of the dietary formulation.

8. The dietary formulation of claim 1, further comprising at least one antioxidant.

9. The dietary formulation of claim 8, wherein the at least one antioxidant is selected from the group consisting of vitamin C, vitamin A, vitamin E, selenium, riboflavin, pyridoxine, and combinations thereof.

10. The dietary formulation of claim 1, further comprising a nonsteroidal anti-inflammatory drug.

11. The dietary formulation of claim 1, wherein the pet food or pet treat is formulated for a dog or cat.

12. The dietary formulation of claim 1, wherein the pet food or pet treat is formulated as a dry, semi-moist, or moist pet food or pet treat.

13. The dietary formulation of claim 12, having a protein content of between about 15% and 30% by weight, and a moisture content less than about 15% by weight.

14. The dietary formulation of claim 12, having a protein content of between about 10% and 30% by weight, and a moisture content less than about 50% by weight.

15. The dietary formulation of claim 12, having a protein content of between about 5% and 20% by weight and a carbohydrate content of between about 15% and 40% by weight.

16. The dietary formulation of claim 1, further comprising at least one of glucosamine or chondroitin.

* * * * *